US011803966B2

(12) United States Patent
Denzinger et al.

(10) Patent No.: US 11,803,966 B2
(45) Date of Patent: Oct. 31, 2023

(54) COMPUTER-IMPLEMENTED METHOD FOR EVALUATING A CT DATA SET REGARDING PERIVASCULAR TISSUE, EVALUATION DEVICE, COMPUTER PROGRAM AND ELECTRONICALLY READABLE STORAGE MEDIUM

(71) Applicant: Siemens Healthcare GmbH, Erlangen (DE)

(72) Inventors: Felix Denzinger, Nuremberg (DE); Sebastian Faby, Forchheim (DE); Max Schoebinger, Hirschaid (DE); Michael Wels, Bamberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 157 days.

(21) Appl. No.: 17/095,057

(22) Filed: Nov. 11, 2020

(65) Prior Publication Data
US 2021/0166389 A1  Jun. 3, 2021

(30) Foreign Application Priority Data

Nov. 28, 2019 (EP) .................................. 19212263

(51) Int. Cl.
*G06V 10/00* (2022.01)
*G06T 7/00* (2017.01)
(Continued)

(52) U.S. Cl.
CPC ............ *G06T 7/0014* (2013.01); *A61B 6/032* (2013.01); *A61B 6/469* (2013.01); *A61B 6/504* (2013.01);
(Continued)

(58) Field of Classification Search
CPC .................................................. G06T 7/0014
See application file for complete search history.

(56) References Cited

U.S. PATENT DOCUMENTS 10,699,407 B2 * 6/2020 Isgum .................... A61B 6/481
11,004,198 B2 * 5/2021 Isgum ................. G06F 18/2411
(Continued)

FOREIGN PATENT DOCUMENTS

CN       109829878 A    5/2019
CN       110428420 A    11/2019
(Continued)

OTHER PUBLICATIONS

Lugauer, Felix et al. "Precise Lumen Segmentation in Coronary Computed Tomography Angiography" Medical Computer Vision: Algorithms for Big Data. MCV 2014. Lecture Notes in Computer Science, vol. 8848. Springer, Cham, https://doi.org/10.1007/978-3-319-13972-2_13.
(Continued)

*Primary Examiner* — Oneal R Mistry
(74) *Attorney, Agent, or Firm* — Harness, Dickey & Pierce, P.L.C.

(57) ABSTRACT

A computer-implemented method is for evaluating a CT data set of a coronary region of a patient regarding perivascular tissue of at least one target blood vessel. In an embodiment, the computer-implemented method automatically determines a centerline of at least the at least one target blood vessel in the CT data set; defines a region of interest as including at least one defined outer region radius around an extension interval of the centerline, the outer region radius being relatively larger than a radius of the at least one target blood vessel; and calculates at least one quantitative value from CT data in the region of interest.

18 Claims, 5 Drawing Sheets

(51) Int. Cl.
  *G06T 7/62* (2017.01)
  *G06T 7/11* (2017.01)
  *G16H 50/30* (2018.01)
  *G16H 70/20* (2018.01)
  *A61B 6/03* (2006.01)
  *A61B 6/00* (2006.01)

(52) U.S. Cl.
  CPC .............. *A61B 6/5217* (2013.01); *G06T 7/11* (2017.01); *G06T 7/62* (2017.01); *G16H 50/30* (2018.01); *G16H 70/20* (2018.01); *G06T 2207/10081* (2013.01); *G06T 2207/30048* (2013.01); *G06T 2207/30101* (2013.01); *G06T 2207/30172* (2013.01)

(56) References Cited

U.S. PATENT DOCUMENTS

| | | |
|---|---|---|
| 2011/0224542 A1 | 9/2011 | Mittal et al. |
| 2017/0046834 A1 | 2/2017 | Itu et al. |
| 2017/0265832 A1 | 9/2017 | Antoniades |
| 2018/0161104 A1* | 6/2018 | Taylor ................... G06T 17/005 |
| 2018/0243033 A1 | 8/2018 | Tran et al. |
| 2019/0150869 A1 | 5/2019 | Passerini et al. |
| 2019/0287276 A1 | 9/2019 | Antoniades et al. |
| 2020/0029830 A1* | 1/2020 | Haase ..................... G16H 50/30 |
| 2020/0305730 A1* | 10/2020 | Denney, Jr. ............ A61B 5/055 |

FOREIGN PATENT DOCUMENTS

| | | |
|---|---|---|
| EP | 3179917 B1 | 3/2019 |
| WO | WO 2015164086 A1 | 10/2015 |
| WO | WO 2018078395 A1 | 5/2018 |

OTHER PUBLICATIONS

Antonopoulos, Alexios S. et al. "Detecting human coronary inflammation by imaging perivascular fat", Science translational medicine, Atherosclerosis, 2017, vol. 9, pp. 1-12.

Lambin, P. et al., "Radiomics: Extracting more information from medical images using advanced feature analysis.", European Journal of Cancer 48 (4), pp. 441-446, 2012.

Zheng, Yefeng et al. "Robust and accurate coronary artery centerline extraction in CTA by combining model-driven and data-driven approaches" MICCAI 2013, Part III, LNCS 8151, pp. 74-81, 2013.

Fuster, V. et al. "The pathogenesis of coronary artery disease and the acute coronary syndromes", New England Journal of Medicine, 1992, vol. 326, Nr. 5, pp. 310-318.

Mendis, S. et al. "Organizational Update The World Health Organization Global Status Report on Noncommunicable Diseases 2014; One More Landmark Step in the Combat Against Stroke and Vascular Disease", Stroke, 2015, vol. 46, e121-e122, DOI: 10.1161/STROKEAHA.115.008097.

European Search Report for European Application No. 19212263.8 dated Mar. 18, 2020.

* cited by examiner

COMPUTER-IMPLEMENTED METHOD FOR EVALUATING A CT DATA SET REGARDING PERIVASCULAR TISSUE, EVALUATION DEVICE, COMPUTER PROGRAM AND ELECTRONICALLY READABLE STORAGE MEDIUM

PRIORITY STATEMENT

The present application hereby claims priority under 35 U.S.C. § 119 to European patent application number EP19212263.8 filed Nov. 28, 2019, the entire contents of which are hereby incorporated herein by reference.

FIELD

An example embodiment of the application generally relates to a computer-implemented method for evaluating a CT data set of a coronary region of a patient regarding the perivascular tissue of at least one target blood vessel, in particular at least one coronary artery. Example embodiment of the application further generally relate to an evaluation device, a computer program and an electronically readable storage medium.

BACKGROUND

It has been found that coronary vascular disease (CVD) is the most common cause of death world-wide, see "Organizational Update: The World Health Organization Global Status Report on Noncommunicable Diseases 2014: One More Landmark Step in the Combat Against Stroke and Vascular Disease" by Stephen Mendis et al., 2015. Most CVDs are related to atherosclerotic coronary artery plaque deposits, which arise due to inflammation or disturbances in the blood flow.

To examine patients regarding CVD and possibly other diseases, it is known to use computed tomography (CT) to obtain a CT data set of the coronary region of the patient, wherein usually a contrast agent is administered to allow for better visibility of the blood vessels, in particular the coronary vessels. This imaging approach in known as coronary computed tomography angiography (CCTA).

Recent research suggests that inflammation in the tissue around the coronary arteries correlates with the mean HU value of the HU range relevant for fatty tissue (−200 HU to 30 HU). A corresponding quantitative value derivable by evaluation of CT data sets was introduced as Fat Attenuation Index (FAI) by the authors of "Detecting human coronary inflammation by imaging perivascular fat", Alexios N. Antonopoulos et al., Science Translational Medicine 9, eaal2658 (2017). In order to measure this value, a concentric perivascular region of interest (ROI) needs to be segmented and the FAI within this area is calculated from the HU value distribution. The ROIs proposed by the authors of the above-named article start 10 mm from the ostium or the branching between the left artery descending (LAD) and the arteria circumflex (CX), have a length of 40 mm and are defined as the area between the outer wall of the blood vessel and a radial distance to the vessel wall. The ROIs need to be located at least partly manually, in particular regarding the outer wall of the blood vessel, which is cumbersome and prone to error.

Moreover, anatomic variants need special handling when calculating these regions of interest. For example, the shepherd's crook in the right coronary artery (RCA), which is defined as a loop directly adjacent to the ostium, causes the standard default 40 mm long ROI to overlap with itself for large perivascular radii and does not in general evaluate the same area of pericardial tissue as for other variants. With a prevalence of around 5% this variant is definitely relevant for evaluation of CT data sets. Also, this definition of ROI does not take into account that the size of the heart varies for each patient.

Furthermore, the fact that the region of interest, which may also be called "perivascular wall", is determined relative to the outer wall requires an exact estimation of the outer wall, which usually is not directly discernible from the CT data set, such that the required manual marking of the outer wall is prone to error.

EP 3 179 917 B1 discloses that concentric perivascular areas of interest relative to the outer wall can be analyzed with respect to the mean radiodensity value in the range of adipose tissue. The ROIs may be defined as 10 mm-50 mm from the ostium along the centerline for the RCA and 0-40 mm along the centerline from the LAD/CX bifurcation. According to the above-cited article of Antonopoulos et al., the mean HU value correlates with coronary inflammation and can be an important risk factor to assess patient specific risk.

SUMMARY

However, the inventors have discovered that both EP 3 179 917 B1 and the article have the following shortcomings:
Anatomical variants of the coronary arteries, which often impact the course of the RCA, are ignored, resulting in different analyzed areas of the pericardial fat for different patients.
When defining the ROIs, the same segment length is used for every patient. However, the hearts of different patients vary in their size, also causing different perivascular areas to be analyzed.
The ROIs are defined as a concentric perivascular wall relative to the outer wall of the vessel, such that an exact outer wall segmentation is required which cannot be performed fully automatically and requires manual interaction.
It remains unclear if FAI is an ideal value to assess inflammations in perivascular tissue.

At least one embodiment of the current invention provides a robust, fully-automated method for the extraction of features regarding perivascular tissue from a CCTA data set, which in particular allows better comparison of the determined quantitative values between patients.

Embodiments are directed to a method, an evaluation device, a computer program and an electronically readable storage medium. Advantageous embodiments are described in the claims.

Features, advantages or alternative embodiments herein can be assigned to the other claimed objects and vice versa. In other words, claims for the devices can be improved with features described or claimed in the context of the methods and vice versa. In the former case, the functional features of the method are embodied by objective units of the device.

In a method, according to at least one embodiment of the invention, at least the following are automatically performed:
determining a centerline of at least the at least one target blood vessel in the CT data set, defining a region of interest as having at least one defined outer region radius around an, in particular patient specific, extension interval of the centerline, the outer region radius being larger than the radius of the target blood vessel, and calculating at least one quantitative value from the CT data in the region of interest.

At least one embodiment of the invention further concerns an evaluation device, comprising at least one processor and at least one storage device, and configured to perform the steps of a method according to at least one embodiment of the invention. All comments and advantages regarding the method according to the invention also apply to the evaluation device and vice versa.

In a particular embodiment, the evaluation device may comprise a first interface for receiving the CT data set, a determination unit for determining the centerline, a definition unit for defining the region of interest and a calculation unit for calculating the at least one quantitative value from the CT data in the region of interest. Further functional units regarding the above discussed embodiments are also conceivable. The evaluation device may further comprise a second interface for outputting the at least one quantitative value.

The evaluation device may form part of a CT device, in particular as or as part of a control device of the CT device.

A computer program according to at least one embodiment of the invention can be loaded into a storage device of an evaluation device and comprises program segments to perform the steps of a method according to at least one embodiment of the invention when the computer program is executed on the evaluation device. The computer program may be stored on an electronically readable storage medium according to at least one embodiment of the invention, on which control information comprising at least a computer program according to at least one embodiment of the invention is stored. The control information is configured such that using the electronically readable storage medium in an evaluation device allows the evaluation device to perform the steps of a method according to at least one embodiment of the invention. The electronically readable storage medium is preferably a non-transitory storage medium, for example a CD ROM.

At least one embodiment is directed to a computer-implemented method for evaluating a CT data set of a coronary region of a patient regarding perivascular tissue of at least one target blood vessel, comprising automatically:

determining a centerline of at least the at least one target blood vessel in the CT data set;

defining a region of interest as including at least one defined outer region radius around an extension interval of the centerline, the outer region radius being relatively larger than a radius of the at least one target blood vessel; and calculating at least one quantitative value from CT data in the region of interest.

At least one embodiment is directed to an evaluation device, comprising:

at least one processor; and at least one storage device, the at least one processor being configured to perform at least a computer-implemented method for evaluating a CT data set of a coronary region of a patient regarding perivascular tissue of at least one target blood vessel, comprising automatically:

determining a centerline of at least the at least one target blood vessel in the CT data set;

defining a region of interest as including at least one defined outer region radius around an extension interval of the centerline, the outer region radius being relatively larger than a radius of the at least one target blood vessel; and calculating at least one quantitative value from CT data in the region of interest.

At least one embodiment is directed to a non-transitory computer program product storing a computer program which, when executed by an evaluation device, configures the evaluation device to perform the method of an embodiment.

At least one embodiment is directed to a non-transitory electronically readable storage medium, storing a computer program which, when executed by at least one processor, configures the at least one processor to execute the computer program to perform the method of an embodiment.

BRIEF DESCRIPTION OF THE DRAWINGS

Other objects and features of the present invention will become apparent from the following detailed description considered in conjunction with the accompanying drawings. The drawings, however, are only principle sketches design solely for the purpose of illustration and do not limit the invention. The drawings show.

DETAILED DESCRIPTION OF THE EXAMPLE EMBODIMENTS

Figure 1:
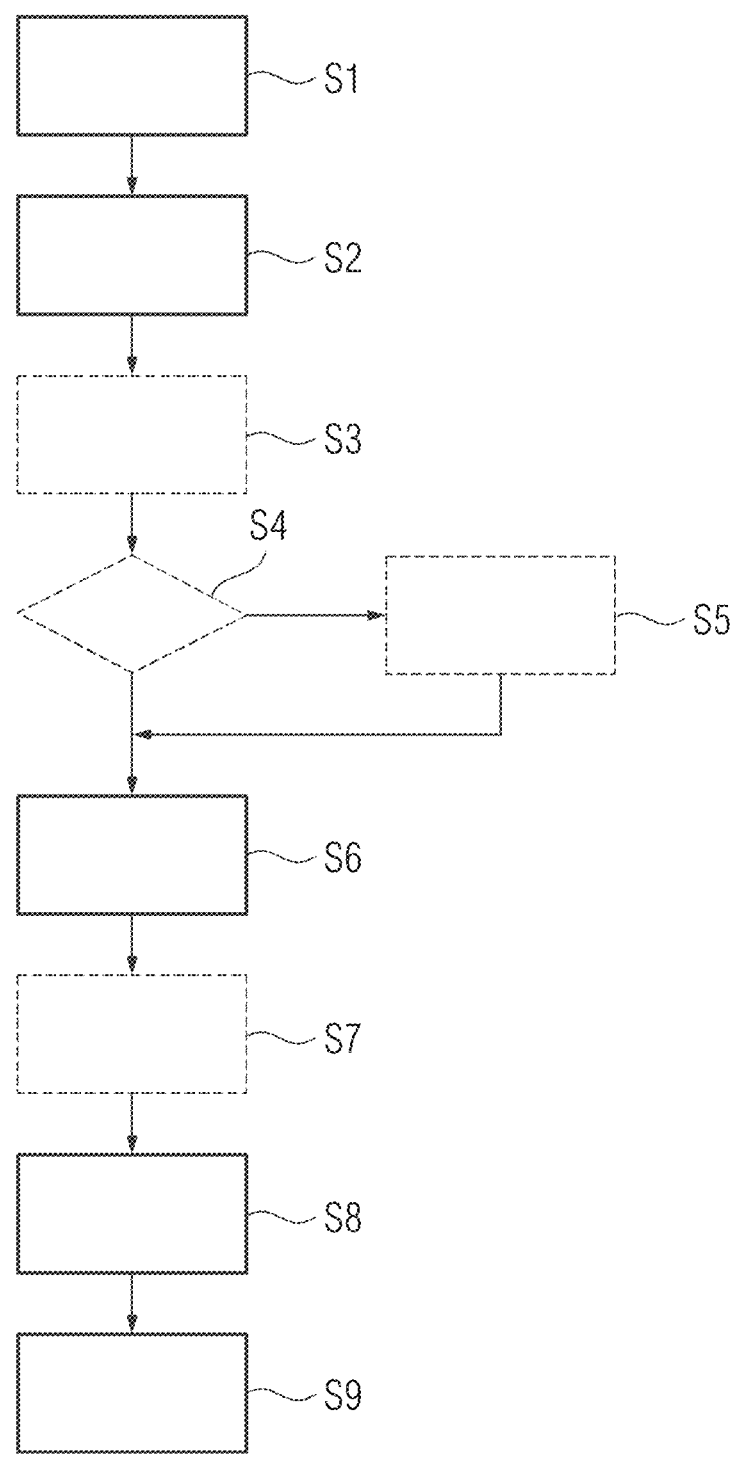
FIG. 1 a flowchart of an embodiment of a method according to an embodiment of the invention, FIG. 2 a schematic curved planar reformation image of a target blood vessel, FIG. 3 a schematic multiplanar reformation image of the target blood vessel, FIG. 4 a sketch showing an alternate option to define an end point of an extension interval, FIG. 5 a principle drawing of a CT device, FIG. 6 the functional structure of an evaluation device according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In a method, according to at least one embodiment of the invention, at least the following are automatically performed:
  determining a centerline of at least the at least one target blood vessel in the CT data set,
  defining a region of interest as having at least one defined outer region radius around an, in particular patient specific, extension interval of the centerline, the outer region radius being larger than the radius of the target blood vessel, and
  calculating at least one quantitative value from the CT data in the region of interest.

The CT data set, which can also be termed CCTA data set, has preferably been acquired using a contrast agent, such that blood vessels, in particular their lumina, may be easily identified and segmented. The CT data set may be acquired using a computed tomography (CT) device, which may also comprise an inventive evaluation device configured to perform the steps of the method according to the invention, for example as or comprised by a control device of the CT device. The evaluation device may, however, also be realised as or as part of a workstation or other computing device.

Regarding the determination of centerlines for blood vessels depicted in the CT data set, suitable algorithms have already been proposed in the state of the art, often based on a segmentation of the lumen of the contrast-filled vessels. For example, the algorithm proposed by Yefeng Zheng et al. in "Robust and Accurate Coronary Artery Centerline Extraction in CTA by Combining Model-Driven and Data-Driven Approaches", in: K. Mori et al. (Eds.): MICCAI 2013, Part III, LNCS 8151, pages 74-81, 2013, the entire contents of each of which are hereby incorporated herein by reference, may be employed.

According to at least one the invention, a new approach for defining the ROIs is proposed. The definition of the ROIs is based on the automatically in a robust and reliable way determinable centerline of the respective target blood vessel, in particular a coronary artery. This obviates the requirement of manual interaction during the definition of the ROIs, allowing a completely automated evaluation process. In especially preferred embodiments, the region of interest is defined as including the vessel wall. Hence, tissue, for example adipose tissue, in the vessel wall, delimited by the inner wall and the outer wall, is also evaluated. Inflamed tissue inside the vessel wall is also relevant, in particular regarding CVD, and is advantageously also considered in the current invention. In the case in which, for example, HU ranges associated with adipose tissue (fatty tissue) and/or water are, in particular exclusively, used to calculate the quantitative values, for example to calculate the FAI, fibrotic and calcified tissue inside the vessel wall are still ignored since their HU values are not included in the range of interest.

Defining the perivascular wall, i.e. the region of interest, using a defined outer region radius around the centerline not only allows faster computation, but is also more robust with respect to segmentation errors, while not impacting the results of the perivascular segmentation. In other words, a fixed (that is, defined with respect to only the centerline) region radius segmentation is far more reliable than a segmentation relative to the (variable and difficult to locate) outer wall.

At least one embodiment of the inventive method allows a fully-automated workflow to extract perivascular tissue features, in particular to detect inflammation around target blood vessels, like coronary arteries, in a further, following step. This allows background evaluation/preprocessing without the need for interaction by a physician.

It is noted at this point that the definition of the region of interest may of course and will usually be target blood vessel specific. That is, for different target blood vessels, for example different coronary arteries, different sizes of the ROIs may be used, in particular different extension intervals and/or different outer region radii.

In general examples, the outer region radius may be about or essentially equal to the target blood vessel radius plus 4 to 10, in particular 5, mm, for example in the interval of 6 to 12 mm (for 2 to 3 mm vessel diameter, e.g.). The length of the extension interval may, for example, be in the range of several tens of millimeters.

The target blood vessels are preferably coronary arteries. In embodiments, at least one target blood vessel is chosen from the group comprising the right coronary artery (RCA), the left artery descending (LAD), the arteria circumflex (CX) and, if existent, the ramus intermedius (RIM). Concrete examples regarding the locations and length of the extension interval for these target blood vessels will be given below regarding concrete embodiments.

Preferably, at least the extension interval, preferably also the region radius, defining the part of the centerline along which the region of interest extends, is defined patient-specific, such that, in particular, different heart sizes of patients can be taken into account and the results exhibit improved comparability.

In a particularly advantageous embodiment, the extension interval and/or the outer region radius are defined by multiplying a predetermined, fixed basis value with a patient specific scaling factor. It has been found in the course of the invention that different patient anatomy, in particular different heart sizes, may be taken into account by using a certain scaling factor, which is determined patient specifically, in particular also from the CT data set. In concrete embodiments, the scaling factor may be determined dependent on the heart size of the patient, in particular from the CT data set and/or as a deviation from a mean heart size of a population of reference patients, wherein the basis value or basis values, respectively, correspond to the mean heart size. The scaling factor is thus determined in a clearly defined, objective measurement, such that even results regarding patients having different heart sizes may be compared. This also possibly impacts clinical studies and research in the field, improving quality and reliability.

For example, the scaling factor may be determined as an absolute or relative extension of the heart, in particular the longest principal axis of the heart, and/or as an absolute or relative linear distance of the beginning and the end of the centerline of at least one of the at least one target vessel, in particular the right coronary artery (arteria coronaria dextra). In the case of a relative extension, for example, the scaling factor may be defined as the ratio between the longest principal axis of the heart for the specific patient and the median value within the population of reference patients (patient cohort). Another option well approximating the heart size is to use the distance between the first (most proximal) and the last (most distal) detected centerline point of a certain blood vessel, preferably the RCA. The latter variant is less preferred, since the last detectable point may depend on image quality and/or used centerline algorithm. Other parameters, in particular if automatically determinable from the CT data set, describing the size of the heart may, however, also be used.

Preferably, in general, both the outer region radius and the extension interval are defined using the scaling factor. Regarding the extension interval, while it is conceivable to scale its length, preferably the starting and end point, in particular as a distance from the ostium, or any parameter for their definition, may both be scaled using the scaling factor.

In concrete embodiments, the extension interval is defined relatively to an ostium marking the beginning of the at least one target vessel, wherein the extension interval begins at a starting point and ends at an end point, wherein the end point is defined either as an extension length from the starting point or distance from the ostium along the centerline, or as the intersection of a circle centered on the ostium and having a defined circle radius with the centerline, wherein in particular the scaling factor is applied in the calculation of the extension length or distance, or the defined circle radius. For example, in a first alternative, the starting point and the end point are both defined as a certain distance along the centerline from the ostium, preferably scaled using the scaling factor. In examples, regarding the RCA, the starting point may be defined as being r*10 mm from the ostium and the end point may be defined as being r*50 mm from the ostium along the centerline, where r is the scaling factor. Regarding the LAD and the CX, r*5 mm and r*45 mm may be used.

It is, however, preferred to use a second alternative, in which the end point is defined according to an intersection between a circle around the ostium and the centerline, for example having a radius of 40 to 60 mm. The advantage here is that anatomical variants, like for example the shepherd's crook, are automatically taken into account, since, for example, when having a loop in the target blood vessel, the length of the extension interval simply increases and it is ensured that the relevant tissue in the circle area is included in any case.

Regarding the definition of the ostium, for at least one of the at least one target blood vessel, the ostium may be defined relatively to a bifurcation of determined centerlines and/or using an at least essentially cylindrical volume model of a larger vessel from which the target blood vessel branches off, in particular the aorta. In many cases, the aorta is modelled cylindrically, that is as a model having a certain volume. In this case, for example for the RCA as target blood vessel, the ostium may be defined as the position where the centerline intersects with the cylindrical volume model or begins from the cylindrical volume model. In other cases, however, for example for the LAD and/or CX, where centerlines bifurcate, the ostium may, for example, be defined as being 0.5 mm downstream from the bifurcation or as a spot where the centerline downstream from the bifurcation has a defined distance from the other centerline, for example 0.5 mm. Regarding the bifurcation of LAD and CX, both are usually used as target blood vessels.

In embodiments, an inner wall of the at least one target vessel can be segmented in the CT data set, wherein an inner region boundary of the region of interest is defined as the respective inner wall location. In this case, the lumen of the target blood vessel is excluded from the region of interest, while the vessel wall is explicitly included with the advantages laid out above. However, in particular if only certain HU ranges are included into the determination of the at least one quantitative value, the lumen does not have to be excluded in any case, since the blood carrying the contrast agent usually has a distinctive HU range. Regarding the automatic segmentation of the inner wall of the vessel wall, that is, the boundary of the lumen, segmentation algorithms already known in the art may be employed. For example, the algorithm proposed by Lugauer et al. in "Precise Lumen Segmentation in Coronary Computed Tomography Angiography", DOI: 10.1007/978-3-319-13972-2_13, September 2014, the entire contents of which are hereby incorporated herein by reference, may be used.

In advantageous embodiments, the outer region radius may be defined as decreasing towards the distal end of the region of interest. For example, a conical region of interest regarding the centerline may be defined using a linearly decreasing outer region radius along the centerline. In this manner, the fact that blood vessels usually become smaller downstream may be considered.

As the quantitative value, at least one radiodensity relating to adipose tissue and/or water or a value derived therefrom may be calculated, in particular for layers of the region of interest along the centerline. For example, a calculation as proposed by Antonopoulos, cited above, may be performed.

In preferred embodiments, however, alternatively or additionally, at least one radiomics algorithm is used to calculate the in particular multiple quantitative values, in particular as a feature vector. In this manner, radiomic features of the perivascular tissue may be extracted using algorithms known in the art, for example from the PyRadiomics open-source library. For more information on radiomics, it may be referred to P. Lambin et al., "Radiomics: Extracting more information from medical images using advanced feature analyzis", European Journal of Cancer 48 (4), 2012, pages 441-446, the entire contents of which are hereby incorporated herein by reference. Using radiomics does not only enable the selection of more suited features than, for example, the FAI, but it also allows the combination of different features, that is, different quantitative values. The extraction of a vast number of features allows for further research topics and also increases the robustness of clinical risk assessment procedures and the prediction of clinical outcomes.

In advantageous embodiments, at least one anomaly detection algorithm for detecting at least one anatomical anomaly in the coronary region may be applied to the CT data set, wherein, if an anatomical anomaly is detected, the definition of the region of interest is modified according to at least one modification instruction associated with the detected anatomical anomaly and/or, if the detected anomaly concerns the presence of at least one predetermined additional blood vessel, the additional blood vessel is added as an additional target blood vessel. For example, if the detected anatomical anomaly concerns the presence of a loop in at least one of the at least one target blood vessel, in particular the presence of a shepherd's crook, the length of the extension interval for the affected target blood vessel is prolonged. In the above-mentioned example for the RCA, wherein the end point of the extension interval is defined as r*50 mm from the ostium when no anomaly is detected, this distance may be increased to, for example r*70 mm or even more. In a like manner, other loops may be handled. It is, however, noted that in the preferred embodiment using a circle around the ostium to find the proximal centerline point having at least a certain absolute distance from the ostium as the end point, such a separate treatment regarding loops is not necessary.

Regarding additional vessels, the additional vessel may be the ramus intermedius (RIM). In some cases, the anatomy shows not only a bifurcation into the LAD and the CX, but a further bifurcation or even a trifurcation, such that a third coronary artery is present, namely the ramus intermedius, which may advantageously be added as an additional target blood vessel, such that all relevant perivascular tissue is examined.

Other examples for anomalies comprise a high take-off, wherein the position of an ostium of a coronary artery is 5 mm or more above the aortic sinotubular junction. Since this anomaly may already be relevant for centerline detection, a corresponding anomaly detection algorithm may be executed before centerlines are determined. Further, a myocardium bridging, i.e. a coronary artery passing through the myocardium instead of through epicardial fat, may be determined by, for example, myocardium segmentation, such that the bridging section may, for example, be excluded from the region of interest.

In concrete embodiments, the anomaly detection algorithm may analyze the course of at least one centerline of at least one of the at least one target blood vessel and/or the structure of a centerline tree comprising the centerline of at least one of the at least one target blood vessel. By analyzing the course of centerlines, loops may be detected, for example the shepherd's crook, while by analyzing the structure of a blood vessel tree, additional blood vessels may be detected. It is also possible that the at least one anomaly detection algorithm comprises at least one artificial intelligence classification algorithm, in particular a neural network, which has been trained by machine learning, in particular deep learning. In particular, a neural network can be a deep neural network, a convolutional neural network, a convolutional deep neural network or a graph convolutional neural network. Furthermore, a neural network can be an adversarial network, a deep adversarial network and/or a generative adversarial network. This is advantageous in the case of more complex anatomical anomalies to be detected. The training data for training the artificial intelligence training algorithm may comprise annotated CT data sets of other patients, wherein in particular at least the presence or absence of the anatomical anomaly is marked.

In preferred embodiments, after defining the region of interest, a user interface allowing modification user input may be displayed and, if modification user input is received, the region of interest may be modified according to the received modification user input. A display, for example a monitor, and an input device, for example a keyboard and/or a mouse, may be used. In this manner, situations wherein the automatic definition of the regions of interest, in particular the definition of the starting and end points and/or the segmentation of the inner wall, is not fully appropriate, for example in cases of unsupported anatomical variations, can be taken into account. The user is enabled to adjust the region of interest, for example the starting and end points of the extension interval, prior to further evaluation. Preferably, the adjustment may be performed in a depiction of the CT data set and/or a schematic view of the vessel tree taken from a segmentation.

The quantitative values may, as already discussed, be further evaluated, in particular by a user, for diagnosis, in particular for diagnosing inflammation in the perivascular tissue.

In a further embodiment, a coronary lesion detection algorithm may evaluate the CT data set, wherein at least one additional region of interest may be defined spanning a detected coronary lesion. In this manner, the analysis is not limited to proximal segments of the target blood vessels, in particular the main coronary arteries, but may be performed for detected coronary lesions, in particular separately for each of those lesions. However, in the case of multiple lesions, at least one quantitative value may also, preferably additionally, be summed up and/or averaged over all lesions. For example, an accumulated FAI may be calculated by summing over all lesions.

At least one embodiment of the invention further concerns an evaluation device, comprising at least one processor and at least one storage device, and configured to perform the steps of a method according to at least one embodiment of the invention. All comments and advantages regarding the method according to the invention also apply to the evaluation device and vice versa.

In a particular embodiment, the evaluation device may comprise a first interface for receiving the CT data set, a determination unit for determining the centerline, a definition unit for defining the region of interest and a calculation unit for calculating the at least one quantitative value from the CT data in the region of interest. Further functional units regarding the above discussed embodiments are also conceivable. The evaluation device may further comprise a second interface for outputting the at least one quantitative value.

The evaluation device may form part of a CT device, in particular as or as part of a control device of the CT device.

A computer program according to at least one embodiment of the invention can be loaded into a storage device of an evaluation device and comprises program segments to perform the steps of a method according to at least one embodiment of the invention when the computer program is executed on the evaluation device. The computer program may be stored on an electronically readable storage medium according to at least one embodiment of the invention, on which control information comprising at least a computer program according to at least one embodiment of the invention is stored. The control information is configured such that using the electronically readable storage medium in an evaluation device allows the evaluation device to perform the steps of a method according to at least one embodiment of the invention. The electronically readable storage medium is preferably a non-transitory storage medium, for example a CD ROM.

FIG. 1 is a flowchart of an embodiment of a method according to the current invention. In this method, a CT data set of an imaging region comprising the heart of a patient is evaluated to derive quantitative values regarding the perivascular tissue. These quantitative values may then, after being provided by the method, be further evaluated, in particular by a physician and/or with respect to CVD.

In a step S1, after administering a contrast agent, the CT data set is acquired using a CT device and CCTA as an imaging method and provided to an evaluation device, which may also be part of the CT device or external to the CT device, for example as or as part of a workstation.

In a step S2, a centerline extraction algorithm and/or an inner wall segmentation algorithm, which may be implemented as a single, common coronary artery segmentation algorithm, are applied to the CT data set to derive the centerlines of coronary arteries, comprising at least the RCA, the LAD and the CX, and, if present, additionally the RIM, and optionally also the inner wall, that is, the edge of the lumen. Since contrast agent was used, this process is robustly executable. For example, the algorithms described in the papers by Zheng et al. and Lugauer et al., as cited above, may be used. The centerlines may, for example, be determined as at least one centerline tree having at least one centerline each and originating from a volume model of the aorta. The inner wall is defined as delimiting the lumen of the vessel with respect to the vessel wall, which also has an outer wall not clearly discernable from the CT data set automatically, that is, by an algorithm.

In step S2, additionally, the heart size of the patient is measured to derive a scaling factor for later use. For example, the longest principal axis of the heart is measured, or the first and last determinable point of the RCA centerline may be used to calculate a direct linear distance between those points. The scaling factor is then calculated as the heart size relative to the mean of a large population of reference patients.

Of the coronary arteries, at least the RCA, the LAD, and the CX are predetermined target blood vessels, whose perivascular tissue is to be automatically examined.

In an optional step S3, anatomic anomalies of the coronary blood vessels may be detected using an anomaly detection algorithm, which may evaluate the centerlines of target blood vessels determined in step S2 and/or the whole CT data set. For example, the presence of loops, like a shepherd's crook of the RCA, may be detected by analyzing the course of centerlines. Additional blood vessels, like the RIM, may be detected by analyzing the vessel tree. The anomaly detection algorithm may employ artificial intelligence, for example comprise a neural network.

In an optional step S4, it is checked whether relevant anatomic anomalies have been detected in step S3. If this is true, in optional step S5, parameters used in following steps for defining a region of interest may be adapted, for example, the length of an extension interval of the region of interest along a centerline may be increased due to loops. In particular, for example in the case of detection of the RIM, additional target blood vessels may be added in step S5.

In step S6, the starting and end points defining an extension interval along the centerline are determined for each target blood vessel, according to target blood vessel specific rules.

In this example embodiment, for the RCA, an ostium is defined as the position where the centerline of the RCA intersects or starts from the wall of the cylindrical volume model of the aorta. From this ostium point, the starting point is defined as lying r*10 mm along the centerline, the end point as lying r*50 mm along the centerline, each from the ostium point. r is the scaling factor determined in step S3, such that the basis values of 10 and 50 mm correspond to the mean heart size of the population of reference patients.

For the LAD and the CX, if present also the RIM, the ostium points are defined as the first proximal point where the centerline is at least 0.5 mm away from the other centerline branching off at the bifurcation. From this ostium point, the starting point is defined as lying r*5 mm along the centerline and the end point is defined as lying r*45 mm along the centerline.

If loops have been detected in step S3, the basis values of 10, 50, 5 and 45 mm may be modified or the determination rule for the end point may be modified, for example as the first, that is most proximal, point along the centerline having a certain direct linear distance to the ostium point, for example 50 mm. In other words, the end point may be chosen as the (most proximal) point where a circle of a certain circle radius (determined as a basis value times the scaling parameter) around the ostium point intersects the centerline.

It is noted at this point that in preferred embodiments the definition of the end point according to a circle centered on the ostium point is used as the only variant, since it leads to the analysis of desired perivascular areas independently of the presence of loops or other course anomalies, such that those anomalies do not have to be detected in optional step S3.

In an optional step S7, which may have been included into step S2 anyways, the lumen and thus the inner wall of each target blood vessel are segmented, as described above. The inner wall location along the centerline in the extension interval defined in step S6 serves a definition for the inner region boundary of the region of interest to be defined.

In step S8, the outer region radius for the region of interest to be defined is determined. In this case, the outer wall of the vessel wall is not used as a reference, but a fixed radius (regarding the circumferential direction) around the centerline is used. The outer region radius may be constant along the extension interval, for example chosen as r*10 mm for the RCA and r*9 mm for the LAD/CX/RIM, that is, a basis value multiplied with the scaling factor as determined in step S2. However, it is also possible that the basis value varies along the extension interval, such that, for example, a conical region of interest with regard to the centerline is defined, wherein the outer region radius decreases in a distal direction.

By the extension interval, the (optional) inner region boundary and the outer region radius, the region of interest for each target blood vessel is clearly and unambiguously defined.

Figure 2:
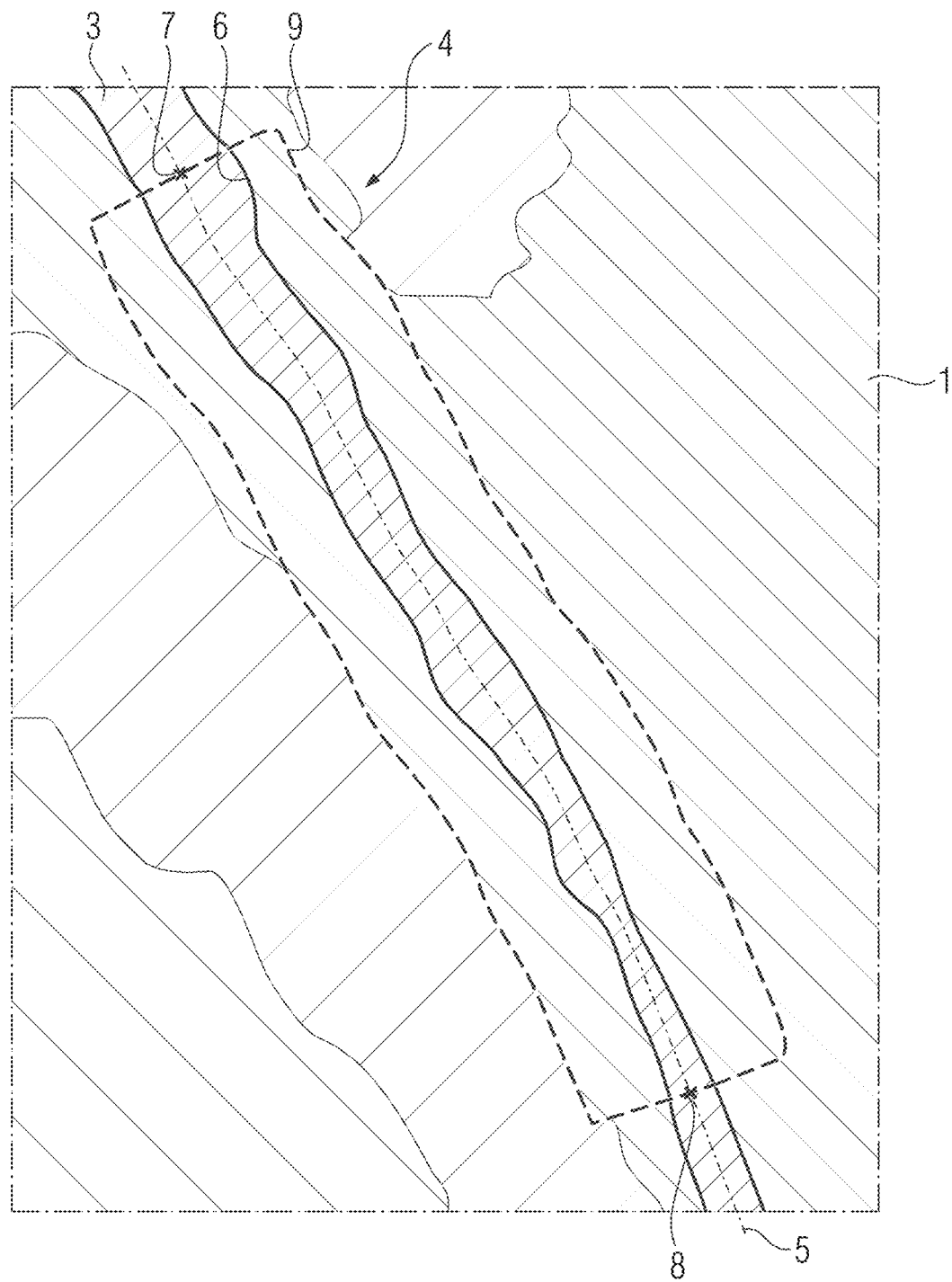
Figure 3:
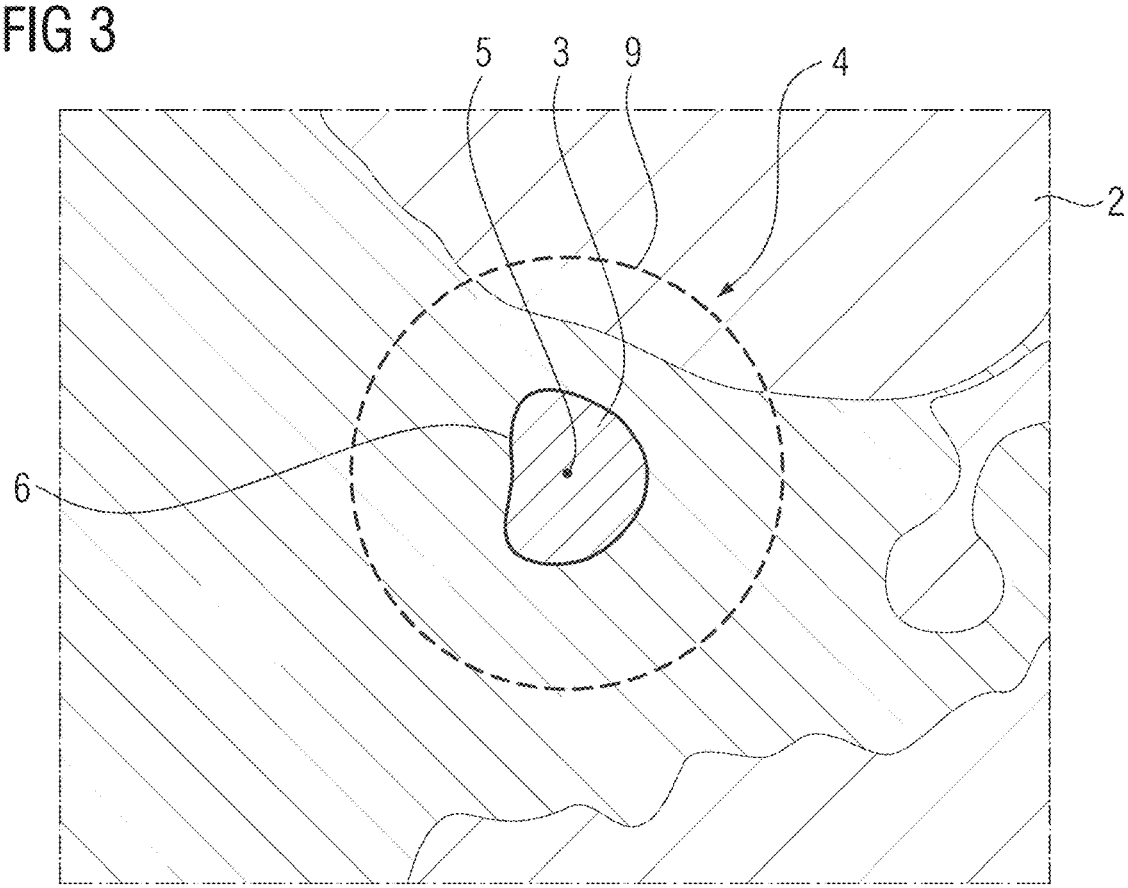

FIG. 2 and FIG. 3 show a schematic CPR 1 and a schematic MPR 2, respectively, of a target blood vessel 3 as well as the defined region of interest 4. The centerline 5 and the inner wall 6, in this embodiment defining the inner boundary of the region of interest 4, are determined in step S2. The starting point 7 and the end point 8 are defined in step S6. As can, in particular, be seen from FIG. 3, in contrast to the inner wall 6, the outer boundary uses a fixed outer region radius 9 around the centerline 5. Only the lumen of the target blood vessel 3 is excluded from the region of interest 4, since the HU values of calcifications and the like in the vessel wall tissue usually lie outside the relevant HU ranges for the following evaluation, for example the HU range for adipose tissue.

Figure 4:
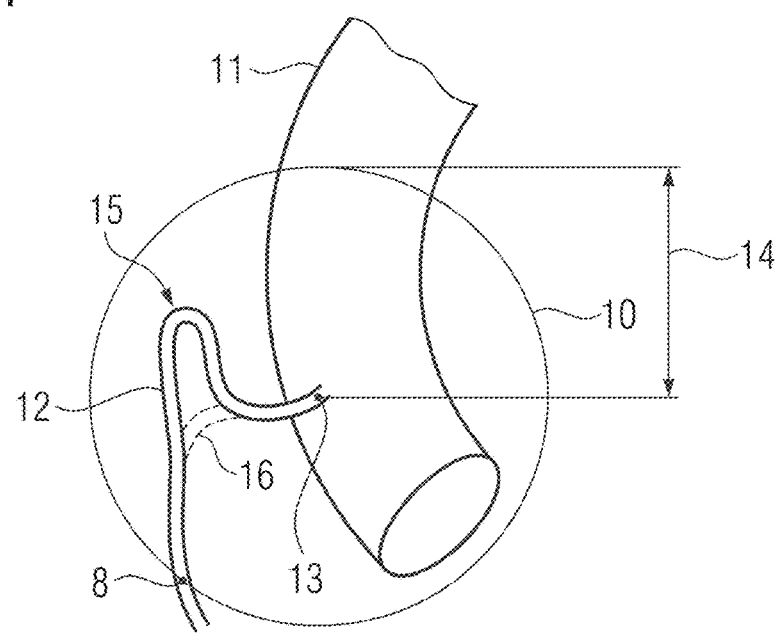

FIG. 4 illustrates the use of a circle 10 to define the end point 8 of the extension interval. A cylindrical volume model 11 of the aorta is indicated. The RCA 12 (and thus its centerline 5) begins at an ostium point 13, which is also the centre of the circle 10 having the circle radius 14. The end point 8 is the most proximal intersection point between the circle 10 and the centerline 5. As can be seen, loops, like the shown shepherd's crook 15, do not influence how far away from the ostium the perivascular tissue will be analyzed. An alternate course 16 of the RCA 12 is indicated for comparison.

Returning to FIG. 1, in a step S9, at least one quantitative value is calculated from the CT data for the perivascular tissue in the region of interest 4 for each target blood vessel 3. While the quantitative value may, for example, be the FAI, it is preferred to apply at least one radiomics algorithm in each region of interest 4. The radiomics algorithm yields a feature vector.

Figure 5:
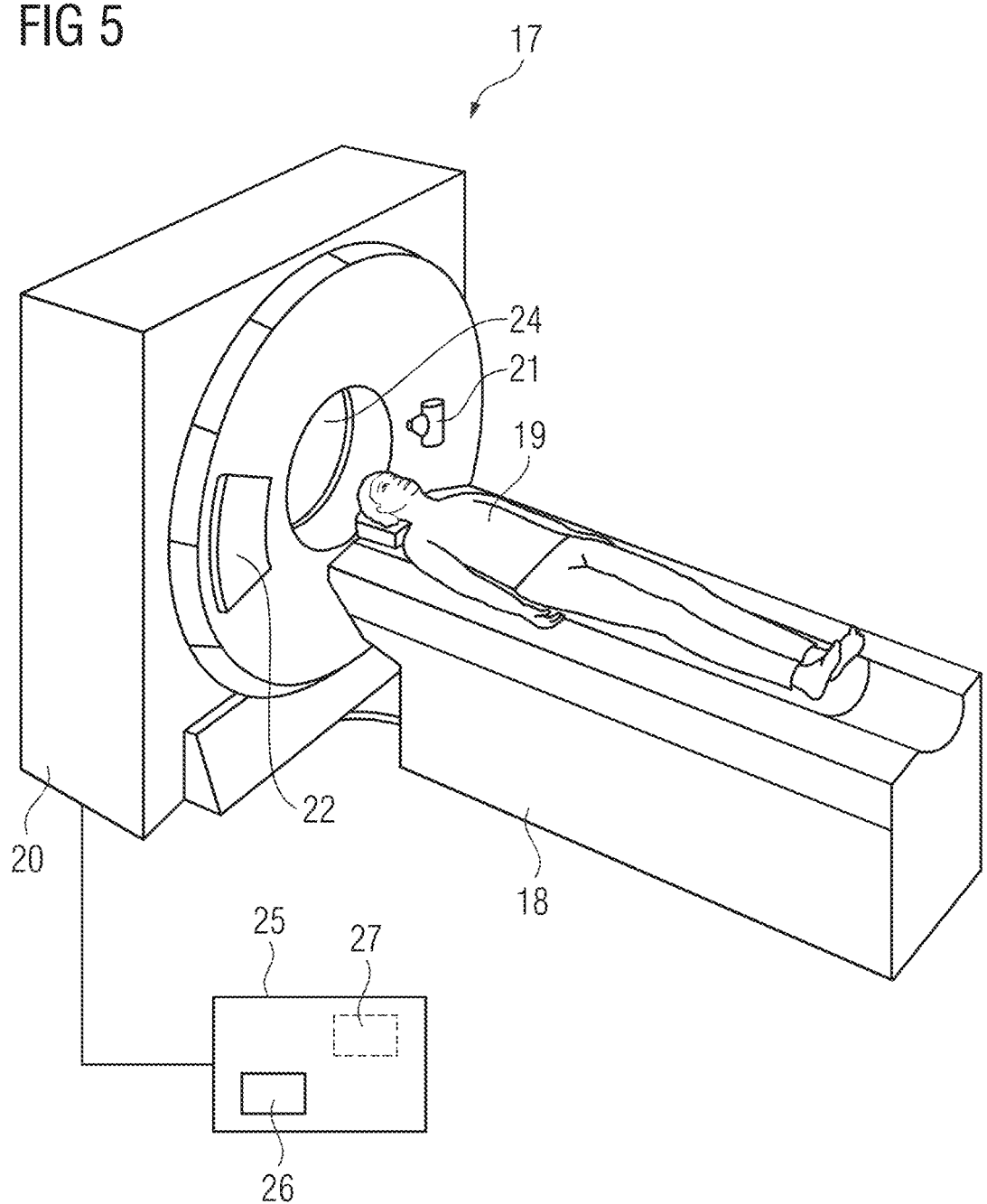

FIG. 5 shows a principle drawing of a CT device 17. The CT device 17 comprises a patient table 18 onto which a patient 19 can be placed. In a gantry 20, an acquisition arrangement comprising an x-ray source 21 and an x-ray detector 22 are rotatably mounted. The patient 19 may be placed inside a patient bore 24, in this case for acquiring CCTA data.

The CT device 17 further comprises a control device 25 having an acquisition unit 26 for controlling the acquisition of CT data, in particular also the CT data set of step S1. As a part of the control device 25, an evaluation device 27 is provided for performing the steps of a method according to an embodiment of the invention.

Figure 6:
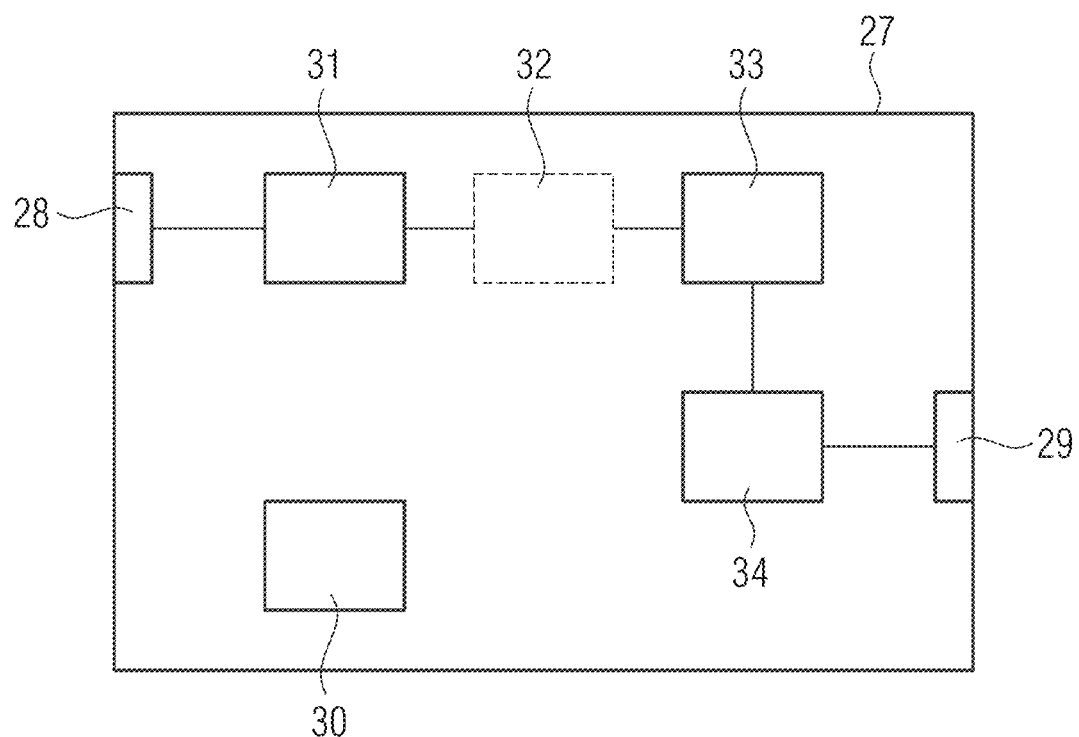

The functional structure of the evaluation device 27 is shown in more detail in FIG. 6. The evaluation device 27 comprises a first interface 28 for receiving the CT data set and a second interface 29 for providing the quantitative values, for example, to a display and/or an external storage additional to an internal storage device 30.

In a determination unit 31, the centerline 5 and the inner wall 6 as well as the heart size are determined according to step S2. An optional anomaly detection unit 32 may be provided for executing the anomaly detection algorithm (step S3) as well as steps S4, S5. The evaluation device 27 further comprises a definition unit 33 for defining the region of interest according to steps S6 to S8 and a calculation unit 34 for calculating the at least one quantitative value from the CT data in the region of interest according to step S9. All functional units 31 to 34 may be implemented on at least one processor (not shown) of the evaluation device 27 and/or as computer program segments of a computer program according to an embodiment of the invention.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for evaluating a CT data set of a coronary region of a patient regarding perivascular tissue of at least one target blood vessel, the computer-implemented method comprising:
    determining a centerline of the at least one target blood vessel in the CT data set;
    defining a region of interest including at least one defined outer region radius around an extension interval of the centerline, the at least one defined outer region radius being larger than a radius of the at least one target blood vessel, wherein at least one of the extension interval or the at least one defined outer region radius are defined by multiplying a fixed basis value with a patient specific scaling factor; and
    calculating at least one quantitative value from the data set in the region of interest.

2. The computer-implemented method of claim 1, wherein the region of interest includes a vessel wall of the at least one target blood vessel.

3. The computer-implemented method of claim 2, wherein
    the patient specific scaling factor is dependent on a size of a heart of the patient, and
    the fixed basis value corresponds to a mean heart size of a population of reference pateints.

4. The computer-implemented method of claim 1, wherein
    the patient specific scaling factor is dependent on a size of a heart of the patient, and
    the fixed basis value corresponds to a mean heart size of a population of reference patients.

5. The computer-implemented method of claim 4, wherein the patient specific scaling factor is determined as an absolute extension of the heart or a relative extension of the heart.

6. The computer-implemented method of claim 5, wherein the patient specific scaling factor is at least one of
    a longest principal axis of the heart, or
    an absolute or a relative linear distance between a start of the centerline and an end of the centerline.

7. The computer implemented method of claim 4, wherein the patient specific scaling factor is determined from at least one of
    the CT data set, or
    as a deviation from the mean heart size.

8. The computer-implemented method of claim 1, wherein the extension interval includes a start point and an end point, the start point and the end point being defined based on an ostium which marks a beginning of the at least one target blood vessel, and the end point being defined as
- an extension length or a distance from at least one of the ostium or the point along the centerline, or
- an intersection between the centerline and a circle having a defined radius centered on the ostium.

9. The computer implemented method of claim 8, wherein the ostium for at least one of the at least one target blood vessel is defined based on at least on of
- a bifurcation of a plurality of centerlines determined for a plurality of target blood vessels, or
- a cylindrical volume model of a larger blood vessel from which the at least one of the at least one target blood vessel branches off.

10. The computer-implemented method of claim 1, wherein
- an inner wall of the at least one target blood vessel is segmented in the CT data set, and
- an inner boundary of the region of interest is defined by the inner wall.

11. The computer-implemented method of claim 1, wherein the at least one defined outer region radius decreases towards a distal end of the region of interest.

12. The computer-implemented method of claim 1, wherein the at least one quantitative value is at least one of
- a radiodensity based on at least one of adipose tissue or water, or
- a value derived from the radiodensity.

13. The computer-implemented method of claim 1, wherein at least one radiomics algorithm is used to calculate multiple of the at least one quantitative value.

14. The computer-implemented method of claim 1, wherein
- at least one anomaly detection algorithm is applied to the CT data set for detecting at least one anatomical anomaly in the coronary region,
- in response to detecting a first anatomical anomaly, the region of interest is modified according to at least one modification instruction associated with the first anatomical anomaly, and
- in response to the first anatomical anomaly being at least one additional blood vessel, the at least one additional blood vessel is added as an additional target blood vessel.

15. The computer-implemented method of claim 1, wherein the region of interest includes at least one defined outer region radius that is around a patient specific extension interval of the centerline.

16. An evaluation device to evaluate a CT data set of a coronary region of a patient regarding perivascular tissue of at least one target blood vessel, the evaluation device, comprising:
- at least one processor; and
- a memory storing computer-executable by the at least one processor, cause the evaluation device to
  - determine a centerline of the at least one target blood vessel in the CT data set,
  - define a region of interest including at least one defined outer region radius around an extension interval of the centerline, the at least one defined outer region radius being larger than a radius of the at least one target blood vessel, wherein at least one of the extension interval or the at least one defined outer region radius are defined by multiplying a fixed basis value with a patient specific scaling factor, and
  - calculate at least one quantitative value from the CT data set in the region of interest.

17. A non-transitory electronically readable storage medium, storing a computer program which, when executed by at least one processor, configures the at least one processor to execute the computer program to perform the computer-implemented method of claim 1.

18. A non-transitory machine readable, medium storing executable instructions that, when executed by at least one processor, causes the at least one processor to perform a method for evaluating a CT data set of a coronary region of a patient regarding perivascular tissue of at least one target blood vessel, the method comprising:
- determining a centerline of the at least one target blood vessel in the CT data set;
- defining a region of interest including at least one defined outer region radius around an extension interval of the centerline, the at least one defined outer region radius being larger than a radius of the at least one target blood vessel, wherein at least one of the extension interval or the at least one defined outer region radius are defined by multiplying a fixed basis value with a patient specific scaling factor; and
- calculating at least ore quantitative value from the CT data set in the region of interest.

* * * * *